(12) United States Patent
Nath et al.

(10) Patent No.: US 6,670,808 B2
(45) Date of Patent: Dec. 30, 2003

(54) SELF REFERENCE EDDY CURRENT PROBE, MEASUREMENT SYSTEM, AND MEASUREMENT METHOD

(75) Inventors: Shridhar Champaknath Nath, Niskayuna, NY (US); Curtis Wayne Rose, Mechanicville, NY (US); Carl Stephen Lester, Clifton Park, NY (US); Thomas James Batzinger, Burnt Hills, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/682,376

(22) Filed: Aug. 27, 2001

(65) Prior Publication Data

US 2003/0038628 A1 Feb. 27, 2003

(51) Int. Cl.[7] .......................... G01B 7/06; G01N 27/72; G01R 35/00
(52) U.S. Cl. .................. 324/230; 324/225; 324/238; 324/202
(58) Field of Search ................. 324/229–242, 324/225, 202; 702/38

(56) References Cited

U.S. PATENT DOCUMENTS

| | | | | |
|---|---|---|---|---|
| 3,441,840 A | * | 4/1969 | Randle | 324/230 |
| 4,095,181 A | * | 6/1978 | Harris et al. | 324/238 |
| 4,450,405 A | * | 5/1984 | Howard | 324/234 |
| 4,459,550 A | * | 7/1984 | Nix nee Saxler | 324/230 |
| 4,695,797 A | * | 9/1987 | Deutsch et al. | 324/230 |
| 4,763,274 A | * | 8/1988 | Junker et al. | 702/38 |
| 5,191,286 A | * | 3/1993 | Fischer | 324/230 |
| 5,371,462 A | | 12/1994 | Hedengren et al. | |
| 5,389,876 A | | 2/1995 | Hedengren et al. | |
| 5,416,411 A | * | 5/1995 | Elsmore | 324/230 |
| 5,442,286 A | | 8/1995 | Sutton, Jr. et al. | |
| 5,467,014 A | * | 11/1995 | Nix | 324/230 |
| 5,510,709 A | | 4/1996 | Hurley et al. | |

(List continued on next page.)

OTHER PUBLICATIONS

D. Hurley, K.H. Hedengren, P.J. Howard, W.P. Kornrumpf, G. E. Sutton and J.D. Young, "An Eddy Current Array System for Aircraft Engine Inspections", Review of Progress in Quantitative Nondestructive Evaluation, Plenum Press, New York, vol. 13, pp. 1111–1118 (1994).

T. Patton, R. Filkins, J. Fulton, K. Hedengren, J. Young, C. Granger and T. Hewton, "Development of a Hand–Held, Flexible Eddy Current Probe for Inspection of Curving Surfaces", Review of Progress in Quantitative Nondestructive Evaluation, Plenum Press, New York, vol. 16, pp. 2107–2111.

(List continued on next page.)

*Primary Examiner*—N. Le
*Assistant Examiner*—Darrell Kinder
(74) *Attorney, Agent, or Firm*—Penny A. Clarke; Patrick K. Patnode

(57) ABSTRACT

A self referencing eddy current probe for determining conductive coating thickness includes a housing having a reference sample area, for accommodating a reference sample, and a testing edge, for positioning on a component during a coating thickness measurement. The eddy current probe further includes a reference eddy current coil situated in the housing adjacent to the reference sample area and a test eddy current coil, which is located at the testing edge. A self referencing eddy current measurement system, for measuring a thickness of a conductive coating on a component, includes the self referencing eddy current probe. The system further includes a signal generator for energizing the test and reference coils and a comparison module for comparing a test signal received from the test coil and a reference signal received from the reference coil and outputting a compared signal.

39 Claims, 9 Drawing Sheets

U.S. PATENT DOCUMENTS

| | | | | |
|---|---|---|---|---|
| 5,659,248 A | * | 8/1997 | Hedengren et al. | 324/242 |
| 5,781,008 A | * | 7/1998 | Muller et al. | 324/230 |
| 5,841,277 A | * | 11/1998 | Hedengren et al. | 324/240 |
| 6,344,741 B1 | * | 2/2002 | Giguere et al. | 324/240 |
| 6,369,565 B1 | * | 4/2002 | Dobler et al. | 324/225 |
| 6,424,151 B2 | * | 7/2002 | Kawata et al. | 324/233 |
| 6,433,541 B1 | * | 8/2002 | Lehman et al. | 324/230 |

OTHER PUBLICATIONS

J. P. Fulton K.H. Hedengren, J.D. Young R. Filkins and T.C. Patton, "Optimizing The Design of Multilayer Eddy Current Probes", Review of Progress in Quantitative Nondestructive Evaluation, Plenum Press, New York, vol. 16, pp. 973–980 (1997).

R.J. Filkins, J.P. Fulton, T.C. Patton and J.D. Young, "Recent Advances and Implementations of Flexible Eddy Current Probe Technology", Review of Progress in Quantitive Nondestructive Evaluation, Plenum Press, New York, vol. 17, pp. 1809–1816 (1998).

B.W. Brusey, J.F. Bussiere, M. Dubois, A. Moreau, "Advanced Sensors for Metals Processing", Proceedings of the International Symposium on Advanced Sensors for Metals Processing, Quebec, Canada, pp. 121–128 (1999).

* cited by examiner

SELF REFERENCE EDDY CURRENT PROBE, MEASUREMENT SYSTEM, AND MEASUREMENT METHOD

BACKGROUND OF THE INVENTION

The invention relates generally to the measurement of coating thickness employing eddy current techniques and, more particularly, to an eddy current probe for measuring the thickness of conductive coatings on conductive substrates, as well as to a measurement system and method using the same.

Components, such as airfoils used for gas and steam turbine power generator applications, include protective coatings that degrade with use. The condition of the coating is critical to the utility of the airfoil. Accordingly, both manufacturers and users must be able to assess the protective coating thickness on the airfoil. Ideally, the coating thickness should be measurable at any point in the service life of the airfoil. In-situ measurements are also important to minimize inspection costs.

For many such components, e.g., the airfoils, both the component and the protective coating are formed of conductive materials. Furthermore, the materials used to form the conductive coating and component often have similar properties.

One example is an airfoil formed of GTD111, a nickel based super alloy, and coated with GT29, a nickel based alloy. Because of their similar properties, it is difficult to distinguish the conductive coating from the conductive component without resort to destructive measurement techniques.

Consequently, the thickness of the conductive, protective coating on conductive airfoils is currently measured by performing metallographic sectioning, which destroys the airfoil. A second method involves weighing the airfoil before and after application of the conductive coating and then using successive weight loss measurements to estimate coating erosion. Although the second method is nondestructive, it is deficient, in that weight loss merely indicates overall coating loss and cannot isolate critical areas, such as the leading and trailing edges of the airfoil. In addition weight measurements also require that the airfoils be removed from the rotor.

Accordingly, it would be desirable to employ a nondestructive measurement technique to determine the thickness of a conductive coating on a conductive component, such as an airfoil. Further, it would be advantageous to provide a measurement technique that can be used to isolate critical areas on the component and that does not require disassembly of the component from its surroundings.

Presently, eddy current inspection provides a nondestructive technique for performing a different class of evaluations, namely the detection of discontinuities or flaws in the surface of various components. See, for example, Hedengren, et al., U.S. Pat. No. 5,389,876, entitled "Flexible Eddy Current Surface Measurement Array for Detecting Near Surface Flaws in a Conductive Part" and Hurley et al., U.S. Pat. No. 5,510709, entitled "Eddy Current Surface Inspection Probe for Aircraft Fastener Inspection and Inspection Method." Briefly, eddy current inspection is based on the principle of electromagnetic induction in which a drive coil is employed to induce eddy currents within the material under inspection, and secondary magnetic fields resulting from the eddy currents are detected by a sense coil, generating signals which are subsequently processed. The drive and sense coil are distinct eddy current coils for differential measurements. For example, oppositely wound drive and sense coils can be used to produce a differential signal. In contrast, the drive and sense coils are provided by the same eddy current coil for absolute measurements.

Eddy current inspection detects flaws as follows. The presence of a discontinuity or a crack in the surface of the component under inspection changes the flow of the eddy currents within the test specimen. The altered eddy current, in turn, produces a modified secondary magnetic field, which is detected by the sense coil, thereby generating a signal which indicates the presence of the flaw upon subsequent processing.

Although this eddy current inspection technique can be extended to measure the thickness of a nonconductive coating on a conductive component, for example, measuring paint thickness on a structure or measuring the thickness of a ceramic coating (thermal barrier coating), this technique is not applicable to conductive coating/conductive substrate combinations. In particular, coating thickness measurements on a nonconductive coating/conductive component combination exploit the fact that the magnetic field generated in the conductive component and detected by an eddy current coil falls off with the thickness of the nonconductive coating. However, this generic methodology is not applicable to conductive coating/conductive substrate combinations because of their similar conductivities.

Accordingly, it would be desirable to develop a measurement technique based on the principle of electromagnetic induction to determine the thickness of a conductive coating on a conductive component, such as an airfoil, in order to exploit the advantages of eddy current inspection. These advantages include: its non-destructive nature and its ability to perform local measurements without removing the component from its environment.

In addition, it would be desirable to develop a sensitive conductive coating thickness measurement technique, which is capable of distinguishing materials having similar electrical properties, such as GTD111 and GT29. It would further be desirable to increase the accuracy of the measurements by providing partial protection from certain environmental factors, such as temperature, pressure, and humidity, which degrade precision.

SUMMARY OF THE INVENTION

Briefly, in accordance with one embodiment of the present invention, a self referencing eddy current probe for determining conductive coating thickness includes a housing having a reference sample area, for accommodating a reference sample, and a testing edge, for positioning on a component during a coating thickness measurement. The eddy current probe further includes a reference eddy current coil situated in the housing adjacent to the reference sample area and a test eddy current coil, which is located at the testing edge.

In accordance with a second embodiment of the present invention, a self referencing eddy current measurement system, for measuring a thickness of a conductive coating on a component, includes a self referencing eddy current probe. The probe includes a housing including a reference sample area, for accommodating a sample, and a testing edge, for positioning on a component during a coating thickness measurement. The probe further includes a test eddy current coil located at the testing edge, and a reference eddy current coil situated in the housing adjacent to the reference sample area.

The self referencing eddy current measurement system further includes a signal generator for energizing the test and reference coils. The self referencing eddy current measurement system also includes a comparison module for comparing a test signal received from the test coil and a reference signal received from the reference coil and outputting a compared signal.

In accordance with a third embodiment of the present invention, a self referencing eddy current measurement method includes positioning an edge of an eddy current probe housing on a test object. The method further includes energizing a test eddy current coil facing the test object, the test coil being situated on an edge of the probe housing. The method also includes energizing a reference eddy current coil facing a reference sample, the reference sample and reference coil being situated in the probe housing. The method further includes comparing a test signal from the test coil with a reference signal from the reference coil to produce a compared signal, and converting the compared signal to a coating thickness value.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
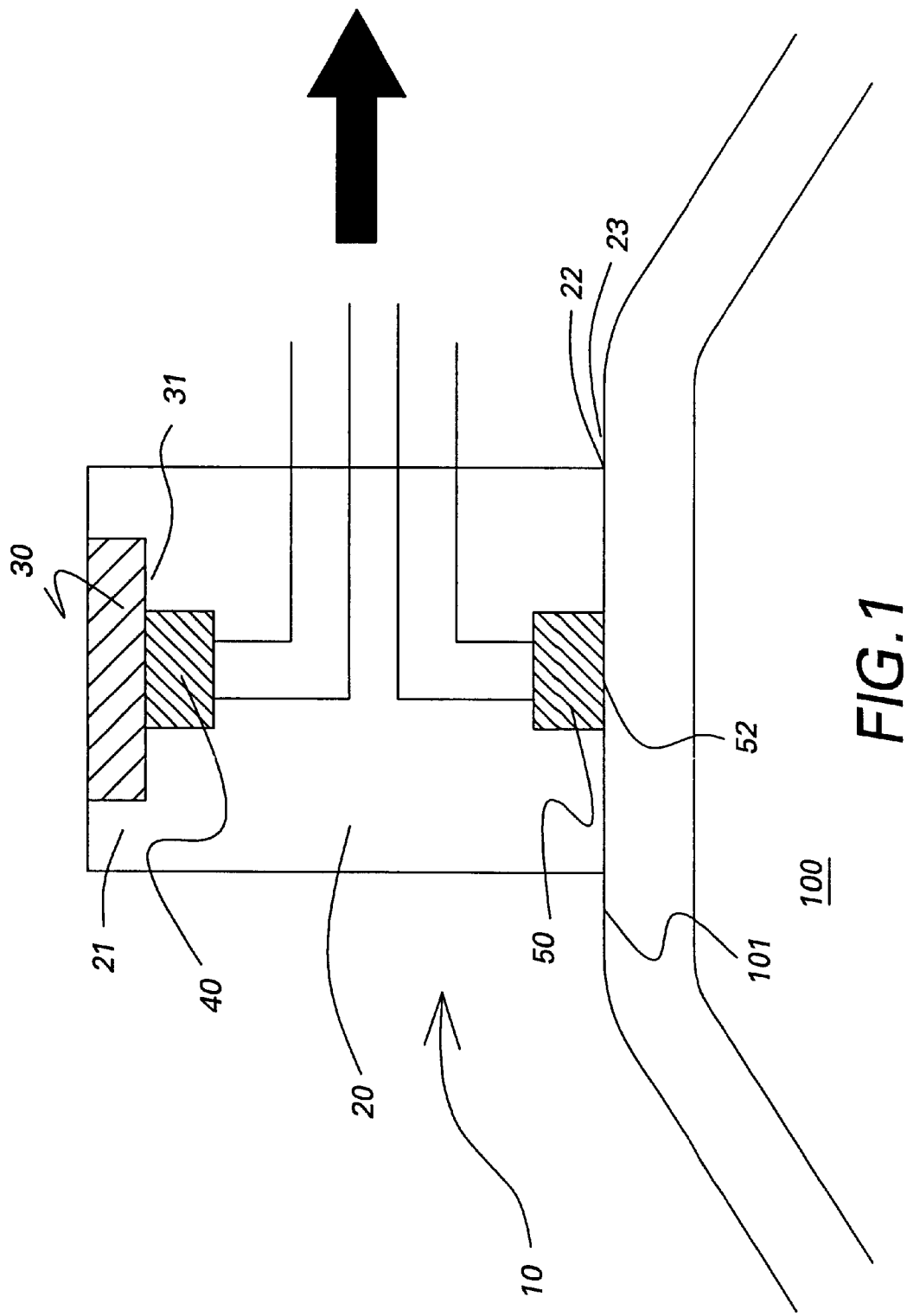
FIG. 1 schematically depicts a self referencing eddy current probe according to a first embodiment of the invention, the probe being positioned on a coated component during a coating thickness measurement.

According to a first embodiment of the invention, a self referencing eddy current probe 10 includes a housing 20, as illustrated schematically in FIG. 1. The housing includes a reference sample area 21 for accommodating a reference sample 30, and a reference eddy current coil 40 is situated in the housing adjacent to the reference sample area. By locating the reference sample area 21 and the reference coil 40 within the housing 20, the effects of ambient conditions, such as temperature, are reduced, thereby increasing the accuracy of the probe 10. The reduction of such external effects aids the performance of sensitive measurements using the probe 10, such as coating thickness measurements where the coating and substrate have similar electrical conductive properties. Exemplary coatings and substrates having similar electrical conductive properties include coatings and substrates formed of metal, for example GTD111 and GT29. These benefits can be achieved by situating the reference sample area 21 anywhere within the housing 20. Accordingly, the placement of the reference sample area depicted in FIG. 1 is purely exemplary and for illustrative purposes only.

Figure 2:
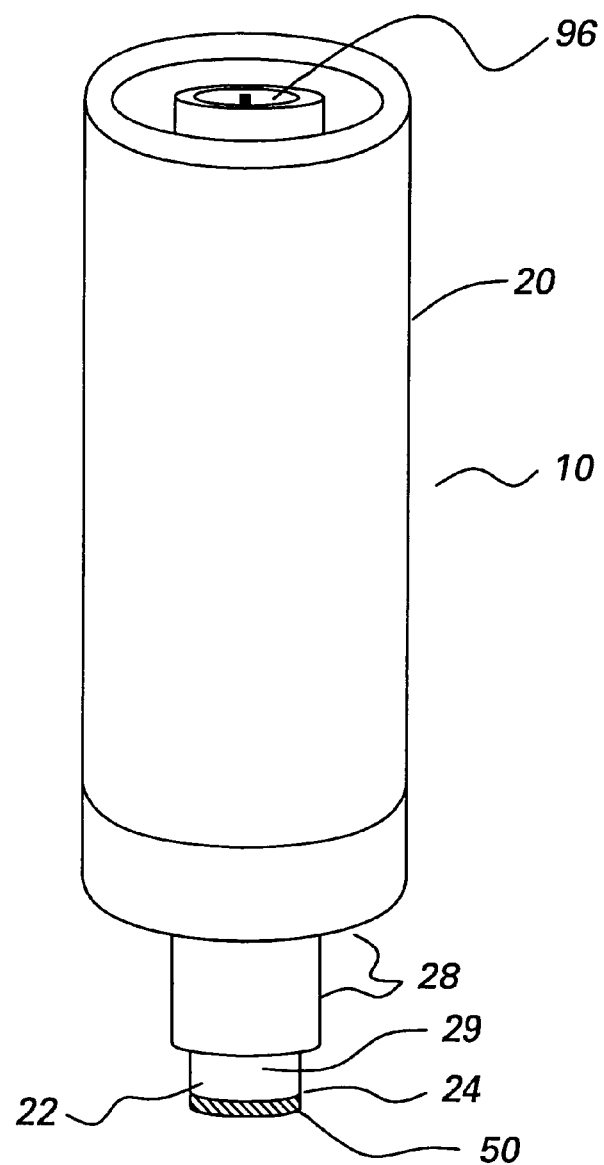
FIG. 2 illustrates an exemplary self referencing eddy current probe according to the first embodiment.

The probe 10 further includes a test eddy current coil 50, which is located at a testing edge 22 of the probe, as exemplarily illustrated in FIG. 2. An active face 52 of the test coil is positioned against a surface 101 of a test object 100 by positioning the testing edge 22 on the test object 100 during a coating thickness measurement.

The testing edge can be situated on any edge of the probe, for example on an end 23 of the housing, as illustrated in FIG. 1 or on an end 24 of a flexible mounting pad 29, as shown in FIG. 2. Preferably, the test coil 50 is flexibly mounted on the probe 10 for conformance to a curved surface portion of the test object 100 during the coating thickness measurement. By conforming the test coil to a surface 101 of the test object, a gap between the test coil and the test object is reduced (preferably providing zero lift-off), thereby increasing measurement precision. Although flexibly mounted test coils are preferred, a rigid test coil mounting will be suitable for some applications, such as performing coating thickness measurements on flat surface areas of test object. Accordingly, the present invention is not limited to flexible test coil configurations but rather encompasses rigid test coil mountings as well.

According to one aspect, the test coil is flexible. Advantageously, the flexible test coil bends to conform to a surface portion of the component during the coating thickness measurement. In this manner, the gap between the component and the test coil is reduced, thereby increasing measurement precision.

According to another aspect, the reference and test coils 40, 50 are single eddy current array probes (SECAPs). SECAPs are single, conducting coils etched on flexible, dielectric substrates, examples of which are illustrated schematically in FIGS. 4 and 5. SECAPs are formed by known photolithographic methods. A variety of conductive materials, such as copper, silver, and gold, and dielectric substrates such as polyimide dielectric films can be used. One exemplary SECAP includes a copper eddy current coil 56 encapsulated on a flexible substrate 57 formed of the material marketed under the trade name Kapton®. In addition, leads 91, 92 can also be formed on the flexible substrate.

The flexible substrate 57 is advantageous in that it conforms to irregular reference sample and test object surfaces 31, 101, reduces probe wobble and lift-off, and efficiently couples the electromagnetic fields to the test object. Preferably the substrate is thin, for example in a range of about 25–100 $\mu$m, with an exemplary SECAP being formed on a 25 $\mu$m thick Kapton® substrate.

Figure 8:
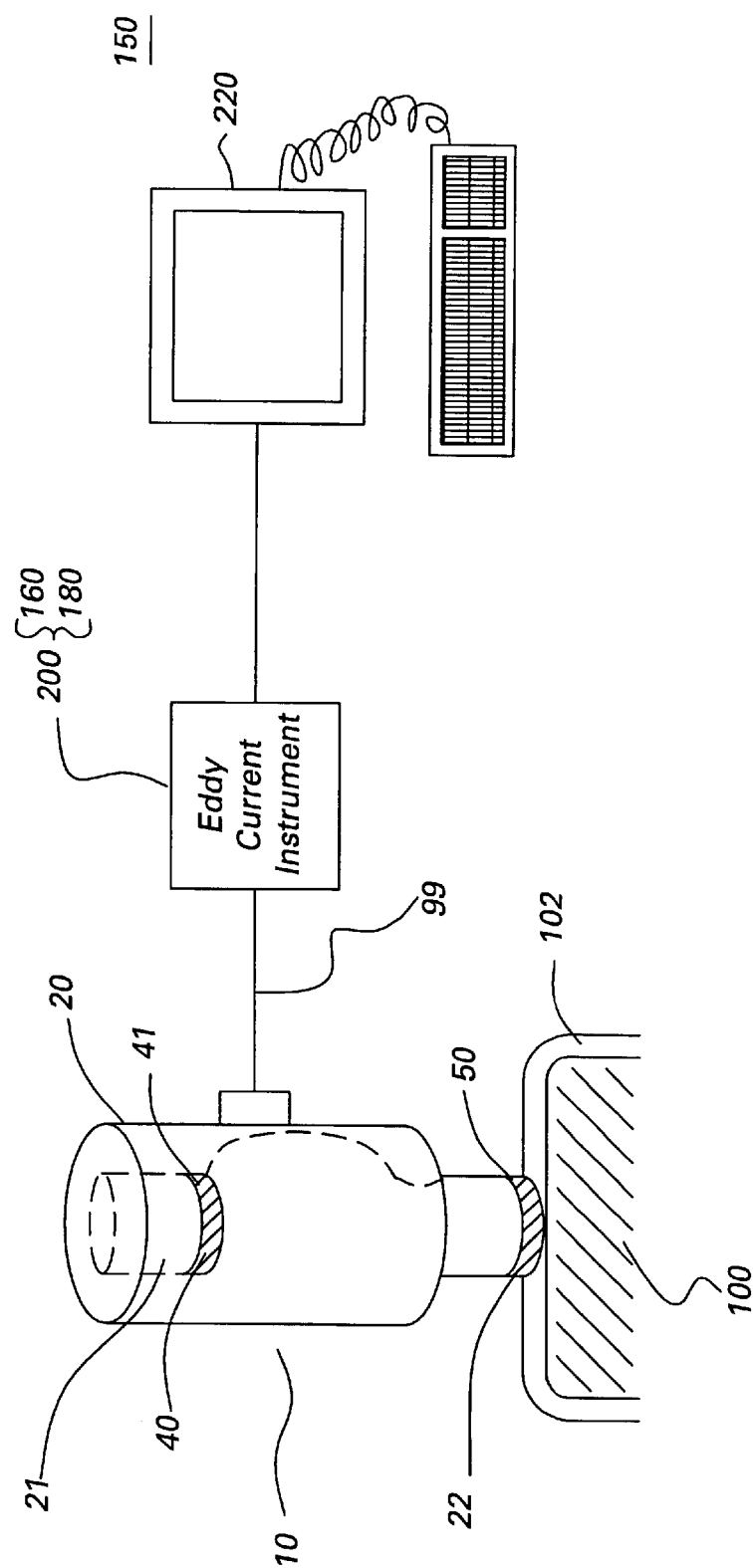
FIG. 8 schematically depicts a self referencing eddy current measurement system which includes an eddy current instrument and a computer.

An additional benefit of SECAPs is that they are compatible with existing eddy current instrumentation, such as an eddy current instrument 200, which is shown in FIG. 8. This Figure schematically illustrates a self referencing eddy current measurement system according to a second embodiment of the invention that is described in detail below.

Figure 4:
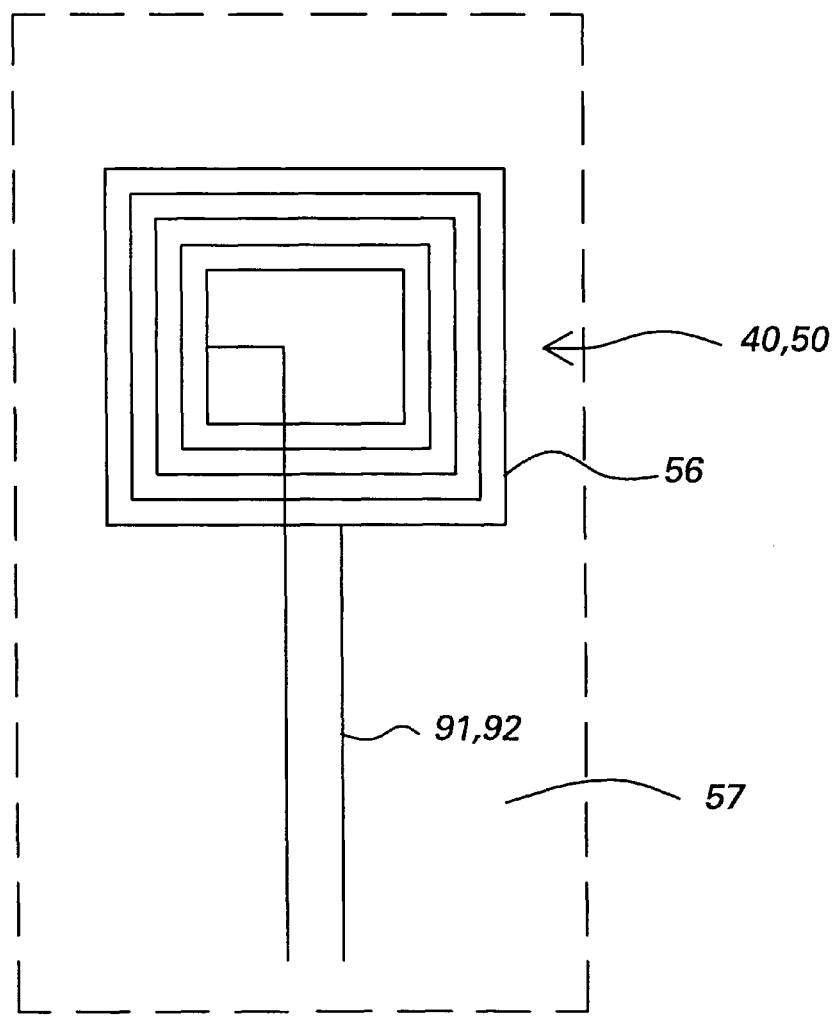
FIG. 4 schematically depicts an absolute single eddy current array probe (SECAP)
Figure 5:
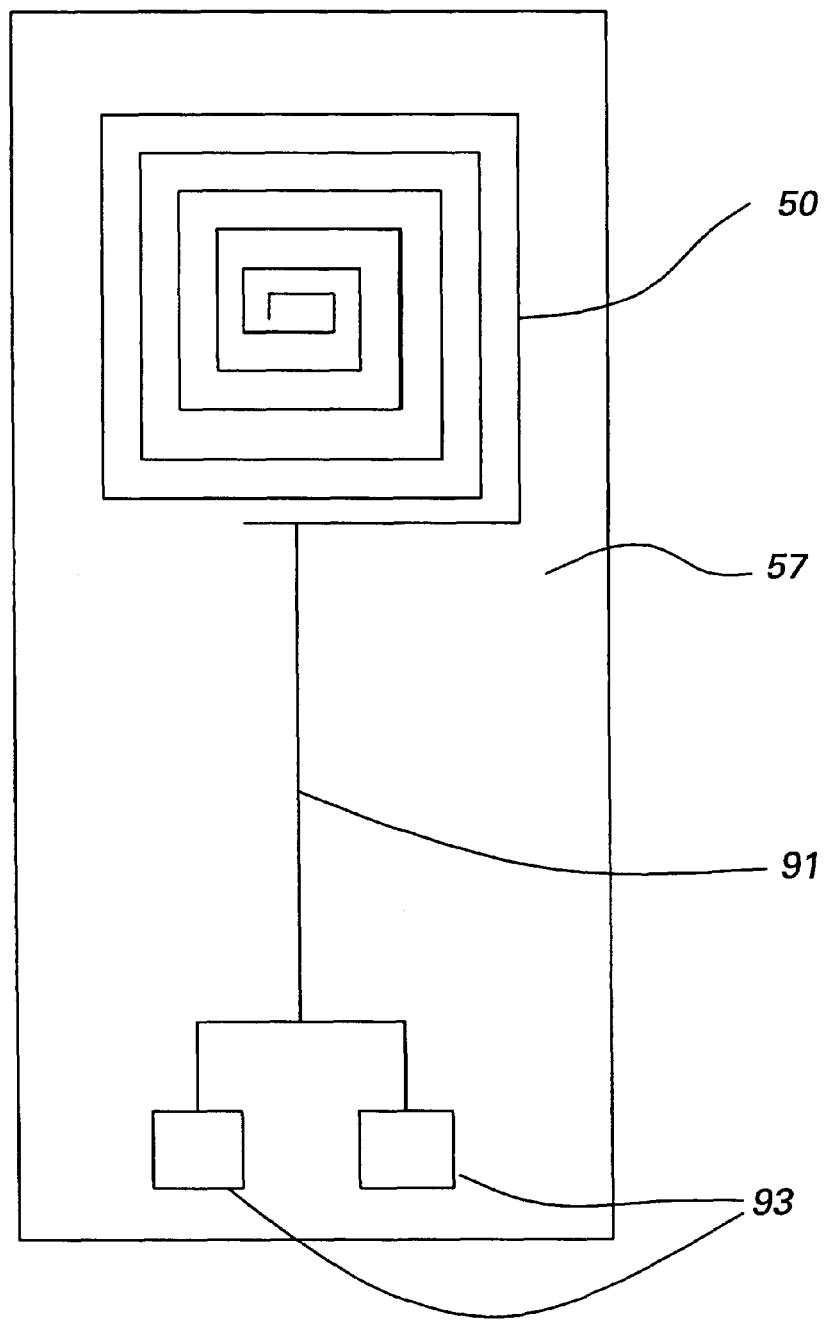
FIG. 5 shows an exemplary absolute SECAP.

According to this aspect, the reference and test coils 40, 50 are preferably absolute SECAPs, as illustrated in FIGS. 4 and 5. Briefly, an absolute SECAP includes one coil 56 that both receives and transmits. Because the coil thus provides a fixed reference for detection, the absolute configuration of the SECAP is useful for thickness calibration.

Figure 7:
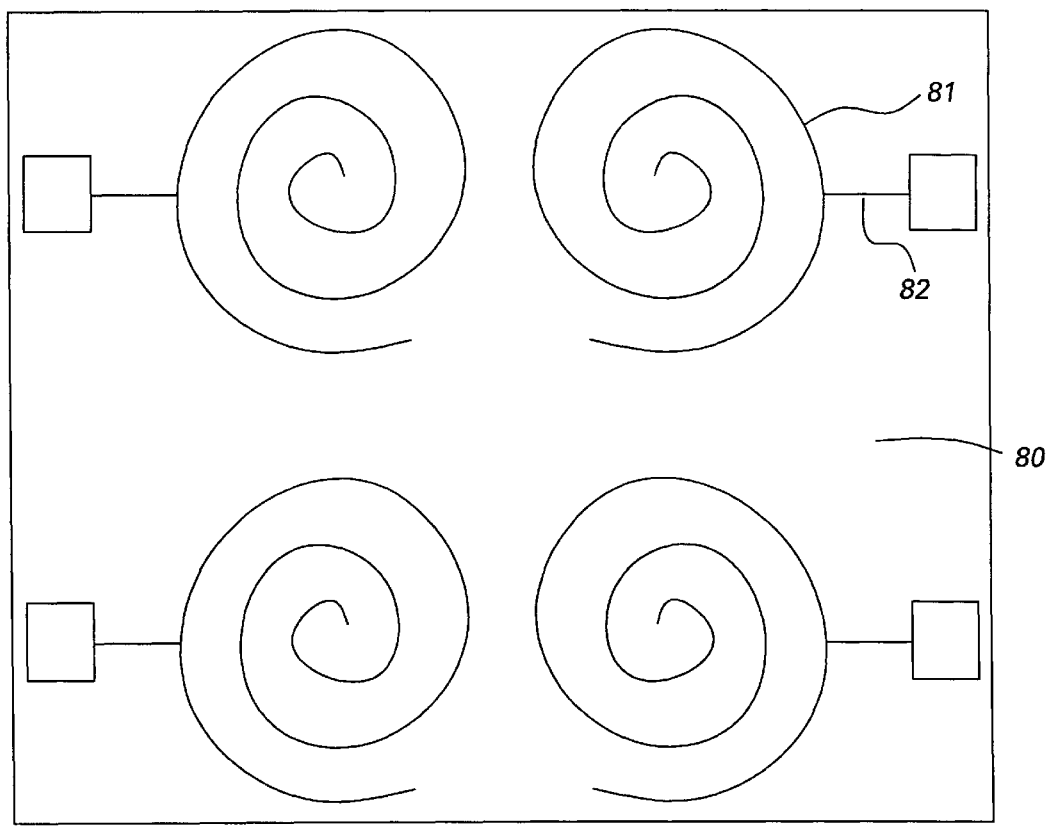
FIG. 7 schematically depicts an exemplary eddy current array probe (ECAP)

According to another aspect, the reference and test coils 40, 50 are eddy current array probes (ECAPs). ECAPs are arrays of conducting coils disposed on dielectric substrates, an example of which is illustrated schematically in FIG. 7. ECAPs are advantageous for applications involving large scanning areas and increased sensitivity. An exemplary ECAP includes 24 differential pick up coils which extend approximately 25 mm, with each coil being about 1.8 mm in length and about 0.9 mm in width. Thus, a single unidirectional scan of an ECAP accommodates inspecting an area covered by the active area of the array.

ECAP's include a flexible substrate 80, upon which a pattern of coils 81 is formed. Exemplary flexible substrates are formed of flexible organic polymers, such as polyimide, one example of which is Kapton®. The coils are formed of conductive materials, examples of which include titanium and copper. Leads 82 can also be formed on the flexible substrate. ECAP's are fabricated using photolithography techniques that are capable of achieving precision and uniformity at small dimensions. An overview of an exemplary fabrication process is provided in U.S. Pat. No. 5,389,876, entitled "Flexible Eddy Current Surface Measurement Array for Detecting Near Surface Flaws in a Conductive Part," by Kristina H. V. Hedengren, et al.

Preferably, the probe 10 further includes a plurality of electrical connections for connecting the test and reference coils 50, 40 to an external device, such as an eddy current instrument 200, as exemplarily illustrated in FIG. 8. The electrical connections preferably include a test lead 91 and a reference lead 92 which are connected to the test and reference coils, respectively, as exemplarily shown in FIG. 3. Where the test and reference coils 50, 40 are formed on flexible substrates 80, 57, such as for ECAPs or SECAPs, the leads 91, 92 are preferably formed on the substrates, as exemplarily shown for a test coil 50 in FIG. 5. For the latter configuration, the leads preferably include test contact pads 93 and reference contact pads (not shown), which are also formed on the flexible substrates, as exemplarily shown in FIG. 5. The electrical connections preferably include an external connector 96, such as the coaxial BNC connector illustrated in FIGS. 2 and 3. Alternatively, a microdot or an amphenol screw type connector or the like can be used to electrically connect the probe 10 to an external device, such as the eddy current instrument 200.

As discussed above, the housing 20 contains the reference coil 40 and reference sample 30. The housing 20 can be made using a variety of materials, based on considerations of cost, convenience, and application. Similarly, the shape and dimensions of the housing will vary based on the application. Moreover, the housing can be formed from a single piece and a single material or alternatively can be formed of several constituent components, the later configuration being shown in cross-sectional view in FIG. 3. Preferably, an inner chamber 25 of the housing is formed of a nonmetallic material, such as plastic, in order to prevent the induction of eddy currents in the inner chamber by the reference coil. Hard plastics are desirable materials for the inner chamber because they are easily machined and are relatively inexpensive. One exemplary hard plastic is sold under the trade name Delrin. More preferably, the inner chamber is enclosed and includes openings 27 for the electrical connections. The openings 27 are indicated schematically in FIG. 3. According to one aspect, the reference coil is bonded to the reference sample, for example by glue, and the reference sample is mounted in the inner chamber using an epoxy potting material, which provides rigidity for mounting.

Figure 3:
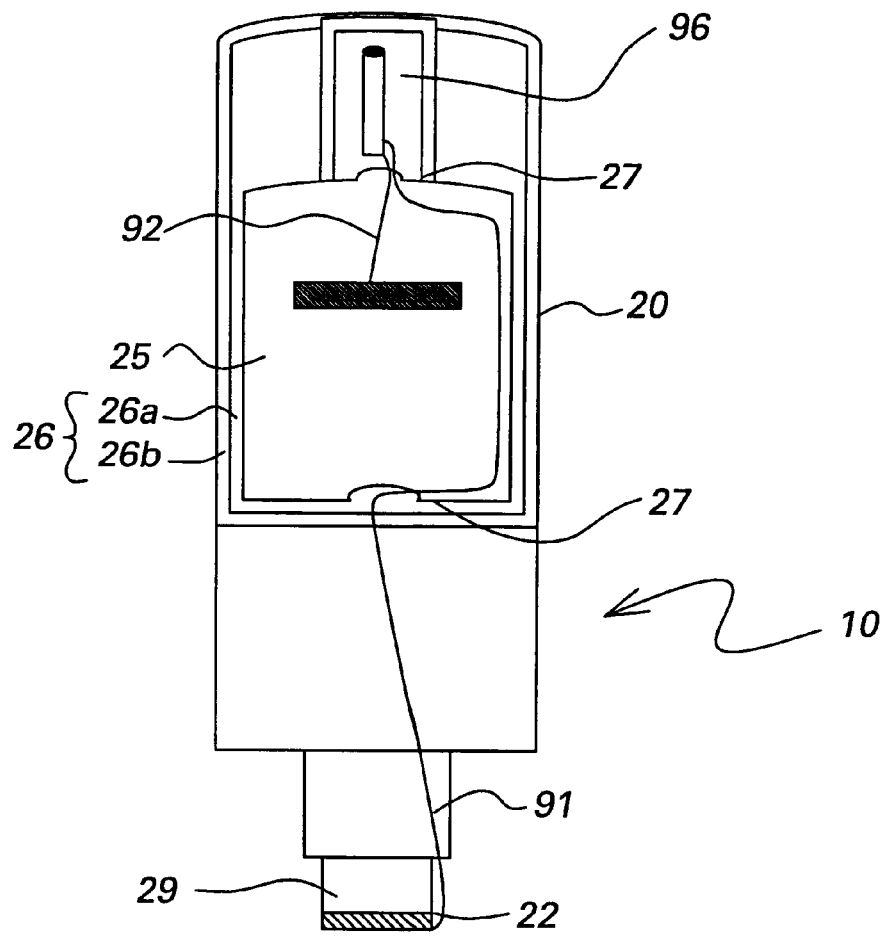
FIG. 3 illustrates the exemplary self referencing eddy current probe of FIG. 2 in cross-sectional view.

Provided the inner chamber insulates the reference coil, the housing may include an outer layer 26 formed of either a metallic or nonmetallic material, as illustrated in FIG. 3. Exemplary outer layer materials include stainless steel, which provides additional magnetic shielding. The outer layer 26 may extend over an external electrical connector 96, as shown in FIG. 3.

The housing may further include a test end component 28, as shown, for example, in FIG. 2. The test coil 50 can be flexibly mounted on the test end component, preferably on an end 24 of a flexible mounting pad 29, as shown in FIG. 2. The flexible mounting pad 29 can be formed of any suitable, nonconductive, compressible material, such as a two-part epoxy or rubber, in order to provide a close fit between the test coil 50 and the surface 101 of the test object 100 during the coating thickness measurement.

As noted above, the shape and dimensions of the housing 20 will vary based on the application. As shown in FIG. 2, the housing can be cylindrical in shape. A cylindrical housing is convenient for machining and permits use of standard eddy current probe housings, such as a barrel housing from Xactex Corp. The dimensions of the housing 20 depend on the type of test and reference coils being used. For example, SECAPs can be relatively small in diameter (e.g., about 0.3 cm), thus the diameter of the inner chamber 25 could be approximately 0.6 cm, where the reference coil 40 is a SECAP. Similarly, the cross section of the flexible mounting pad 29 should be selected to accommodate that of the selected test coil 50, whether an ECAP, SECAP, or other coil type.

Figure 6:
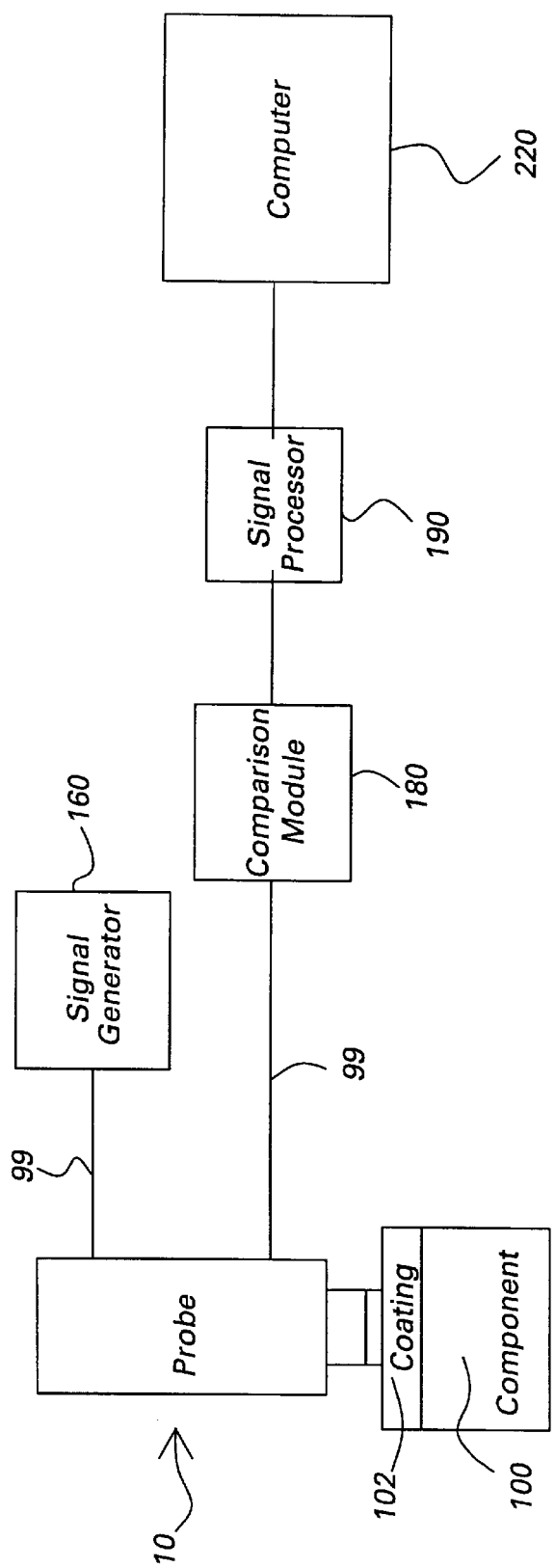
FIG. 6 schematically depicts a self referencing eddy current measurement system according to a second embodiment of the invention.

According to a second embodiment of the invention, a self referencing eddy current measurement system 150 for measuring a thickness of a conductive coating 102 on a conductive component 100 includes a self referencing eddy current probe 10, as illustrated in highly schematic form in FIG. 6. As described above and shown, e.g., in FIG. 1, the eddy current probe includes a housing 20 having a reference sample area 21 for accommodating a reference sample 30, and a reference eddy current coil 40 is situated in the housing adjacent to the reference sample area. The probe further includes a test eddy current coil 50, which is located at a testing edge 22 of the probe. As discussed above with respect to the first embodiment, preferred test and reference coils include SECAPs and ECAPs.

The self referencing eddy current measurement system 150 further includes a signal generator 160, as schematically illustrated in FIG. 6, which energizes the test and reference coils 50, 40. A comparison module 180 compares signals received from the test and reference coils and outputs a compared signal. One exemplary comparison module is a differential amplifier.

The signal generator 160 preferably supplies an AC signal to test and reference coils 50, 40, causing the test and reference coils to emit a test and a reference magnetic field, respectively. The test and reference magnetic fields induce test and reference eddy currents in the test object 100 and reference sample 30, respectively.

SECAP test and reference coils 50, 40 can be energized by signals having amplitudes of about 5–10 V and frequencies in the range of about 500 KHz to 6 MHz. Preferably, the energizing signals have amplitudes of approximately 5 V and frequencies of about 1–3 MHz, for SECAP coils. The energizing frequency depends on the conductivity and the thickness of the coatings. For example, for an average conductivity of $5.8 \times 10^6$ Siemens/meter and a coating thickness of about 0.03 cm, a preferred frequency is approximately 1.5 MHz. Generally, lower frequencies might be used for higher thickness ranges and higher frequencies for thinner coatings.

The comparison module 180 is standard and hence will not be described in detail.

Preferably, the comparison module compares the signals received from the reference and test coils by subtracting a DC amplitude of the reference signal from a DC amplitude of the test signal to produce the compared signal. According to a first aspect, the comparison module is provided by an eddy current instrument, as indicated schematically in FIG. 8. According to a second aspect, the signal generator is also provided by the eddy current instrument, as indicated schematically in FIG. 8. A test lead 91, a reference lead 92, and a connector 96 are provided for electrically connecting the reference and test coils to the eddy current instrument. See, for example, FIG. 3. Although the leads can be external to the test and reference coils, for coils formed on a flexible substrate 57, 80 such as SECAPs and ECAPs, preferably leads are formed in part on the substrates, as illustrated in FIG. 4. External leads 99 extend from the connector to the eddy current instrument or other signal generator and signal receiver.

According to a third aspect, the self referencing eddy current measurement system 150 further includes a signal processor 190, shown schematically in FIG. 6, which is adapted to convert the compared signal to a coating thickness value. As used here, the phrase "adapted to" indicates that the signal processor processes the compared signal in accordance with an algorithm to provide the coating thickness value. More generally, the phrase "adapted to" is used herein to describe a component that processes an input signal in accordance with an algorithm to provide a desired output. One exemplary signal processor is a computer 220, as illustrated in FIG. 8.

Moreover, exemplary means for converting the compared signal to the coating thickness value include using a calibration curve or a plurality of calibration data. The calibration curve or calibration data may either be stored in or accessed externally by the signal processor 190.

According to a fourth aspect, the self referencing eddy current measurement system 150 further includes a computer 220, as illustrated in FIG. 8. The computer can be used to control the signal generator 160, as indicated in FIG. 8.

Figure 9:
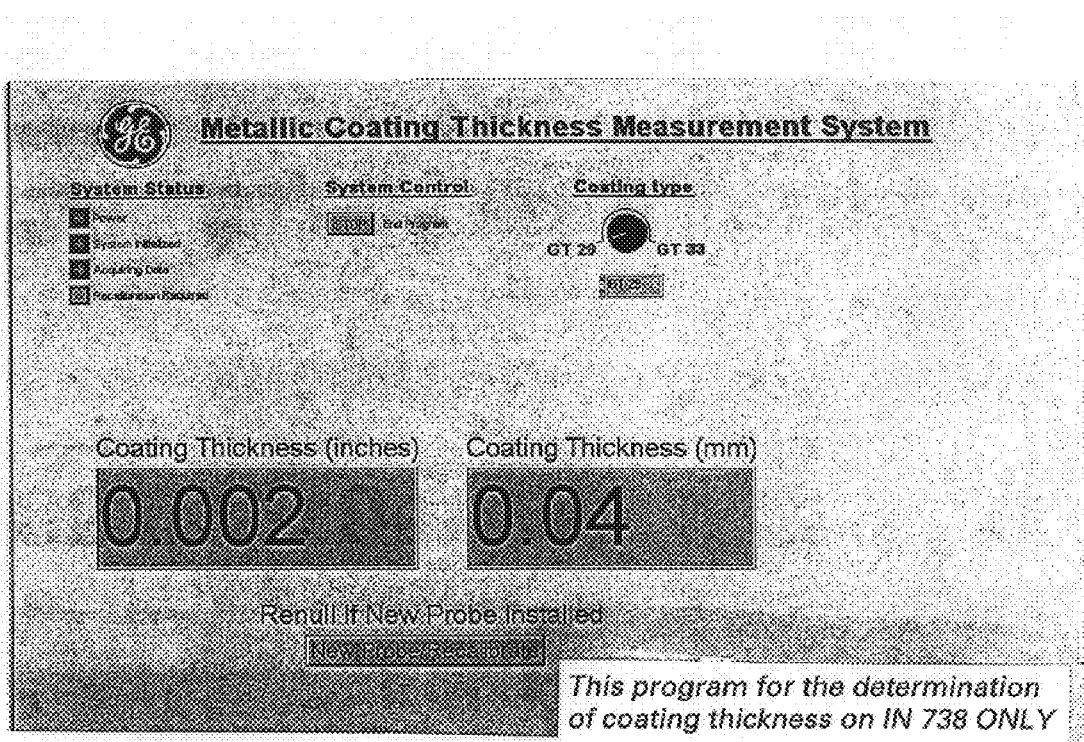
FIG. 9 shows an exemplary computer display, which displays a coating thickness value.

In addition the computer 220 can be configured to receive the compared signal from the comparison module 180, to convert the compared signal to a coating thickness value, and to display the coating thickness value. An exemplary computer display is shown in FIG. 9, which displays the coating thickness value in inches and millimeters. The computer can be used to store a plurality of calibration data and to fit the calibration data to a calibration curve for conversion of the compared signal to a coating thickness value.

Alternatively, the computer 220 can be used to compare the coating thickness value with a cutoff thickness value for performing a coating thickness quality control operation. For example, the computer could store a minimum or a maximum cutoff thickness value (or both minimum and maximum cutoff values) and determine whether the coating thickness value is above the minimum or below the maximum (or both). The computer could then display whether the coating thickness was acceptable or not. Exemplary cutoff values include measured or calibrated cutoff thickness values.

According to a fifth aspect, a reference sample 30 is positioned in the reference sample area 21, and an active reference face 41 is positioned on the reference sample, as illustrated in FIG. 8.

According to a third embodiment of the invention, a self referencing eddy current coating thickness measurement method includes positioning an edge of an eddy current probe housing on a test object, where a test eddy current coil is situated on the edge of the probe housing, as shown, for example, in FIG. 1. Preferably, an active face of the test coil is conformed to a surface of the test object, upon positioning of the edge of the probe housing. The method further includes energizing both the test eddy current coil and a reference eddy current coil facing a reference sample, where the reference sample and reference coil are situated in the probe housing. As discussed above, the test and reference coils can be energized by application of an AC signal, having an amplitude of about 5–10 V and a frequency of about 500 kHz–6 MHz.

The method further includes comparing a test signal from the test coil with a reference signal from the reference coil to produce a compared signal, and converting the compared signal to a coating thickness value. The test and reference signals can be compared by subtracting a DC amplitude of the reference signal from a DC amplitude of the test signal to obtain the compared signal.

According to a second aspect, the self referencing eddy current coating thickness measurement method further includes calibrating the test and reference coils by measuring an uncoated sample and a plurality of coated samples, with each coated sample having a known coating thickness. Calibration includes measuring the uncoated sample using the reference coil, while measuring the coated samples using the test coil. Using the above described method, a compared signal is generated for each coated sample. In this manner, a plurality of calibration data is generated. If desired, the measurement method can further include deriving a calibration curve from the calibration data. Derivation of the calibration curve can be performed using any suitable curve fitting technique, such as a polynomial interpolation function. Conversion of the compared signal to the coating thickness value can be performed using either the calibration curve or the plurality of calibration data.

As noted above, eddy current coils, such as SECAPs and ECAPs, are sensitive to environmental effects, such as temperature and humidity. In addition, the electronics in the eddy current instrument drift with time. As a result, the accuracy of the calibration data tends to decrease with time. Accordingly, it is often desirable to recalibrate the test and reference coils, preferably at a predetermined time interval. For example, depending on the application and environment, a probe with SECAP test and reference coils might be recalibrated every two, four, or eight hours. However, the time interval will be determined based on desired accuracy, application, and environment, for example, and consequently can vary significantly. Recalibration of the test and reference coils is accomplished by repeating the calibration steps set forth above.

According to a third aspect, the self referencing eddy current coating thickness measurement method includes comparing the coating thickness value with a cutoff value to determine whether a coating layer on the test object satisfies a predetermined thickness condition. For example, the coating thickness value may be compared with a minimum (maximum) cutoff value, to determine whether the coating layer is thick (thin) enough. Alternatively, the coating thickness value may be compared with both the minimum and maximum cutoff values, in order to determine whether the coating layers falls within an acceptable thickness range.

According to a fourth aspect, the self referencing eddy current coating thickness measurement method further includes displaying the coating thickness value. The value may be displayed numerically or graphically, for example on a computer screen, on a multimeter display, on an eddy current instrument display, on paper, etc. An exemplary numerical, computer display is shown in FIG. 9. Alternatively, the measurement method may include displaying a result of comparing the coating thickness value with the cutoff value. For example, the words "ACCEPTABLE" or "UNACCEPTABLE" might be displayed. Similarly, the difference between the coating thickness value and the cutoff value might be displayed.

According to a fourth aspect, the self referencing eddy current coating thickness measurement method further includes using a computer to control the energization of the test and reference eddy current coils. For example, the computer could be used to control a signal generator or eddy current instrument, in order to control the timing, amplitude, and frequency of the AC signal applied to the test and reference coils. The measurement method can further include using the computer to compare the test and reference signals to obtain the compared signal, using the computer to convert the compared signal to the coating thickness value, and using the computer to display the coating thickness either graphically or numerically.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A self referencing eddy current probe comprising:
   a housing including a reference sample area, for accommodating a reference sample, and a testing edge, for positioning on a component during a coating thickness measurement;
   a test eddy current coil located at the testing edge; and
   a reference eddy current coil situated in said housing adjacent to the reference sample area.

2. The self referencing eddy current probe of claim 1, wherein said test coil is flexible for conformance to a surface portion of the component during the coating thickness measurement.

3. The self referencing eddy current probe of claim 1, wherein said test and reference coils comprise single eddy current array probes (SECAPs).

4. The self referencing eddy current probe of claim 1, wherein said test and reference coils comprise eddy current array probes (ECAPs).

5. The self referencing eddy current probe of claim 1, further comprising:
   means for electrically connecting said test and reference coils to an eddy current instrument.

6. The self referencing eddy current probe of claim 1, wherein said housing comprises a non-metallic material.

7. The self referencing eddy current probe of claim 6, wherein said housing comprises a plastic material.

8. The self referencing eddy current probe of claim 6, wherein said housing comprises a polymeric material.

9. A self referencing eddy current measurement system for measuring a thickness of a conductive coating on a component, said system comprising:
   a self referencing eddy current probe including:
     a housing including a reference sample area, for accommodating a sample, and
     a testing edge, for positioning on a component during a coating thickness measurement,
     a test eddy current coil located at the testing edge, and
     a reference eddy current coil situated in said housing adjacent to the reference sample area;
   a signal generator for energizing said test and reference coils; and
   a comparison module for comparing a test signal received from said test coil and a reference signal received from said reference coil and outputting a compared signal.

10. The self referencing eddy current measurement system of claim 9, further comprising:
    a signal processor for converting the compared signal to a coating thickness value.

11. The self referencing eddy current measurement system of claim 10, wherein said signal processor is adapted to use a calibration curve to convert the compared signal to the coating thickness value.

12. The self referencing eddy current measurement system of claim 9, further comprising:
    a reference sample positioned in the reference sample area,
    wherein said reference coil includes an active reference face positioned on said reference sample.

13. The self referencing eddy current measurement system of claim 9, wherein said test coil is flexible for conformance to the surface portion of the component during the coating thickness measurement.

14. The self referencing eddy current measurement system of claim 9, wherein said test and reference coils comprise single eddy current array probes (SECAPs).

15. The self referencing eddy current measurement system of claim 9, wherein said test and reference coils comprise eddy current array probes (ECAPs).

16. The self referencing eddy current measurement system of claim 12, further comprising:
    an eddy current instrument, wherein said eddy current instrument includes said signal generator and said comparison module,
    wherein said test and reference coils comprise single eddy current array probes (SECAPs).

17. The self referencing eddy current measurement system of claim 9, wherein said housing comprises a plastic material.

18. The self referencing eddy current measurement system of claim 9, further comprising:
    a computer for controlling said signal generator.

19. The self referencing eddy current measurement system of claim 18, wherein said computer is adapted to receive the compared signal and to convert the compared signal to a coating thickness value.

20. The self referencing eddy current measurement system of claim 19, wherein said computer is adapted to display the coating thickness value.

21. The self referencing eddy current measurement system of claim 19, wherein said computer is adapted to compare the coating thickness value with a cutoff thickness value for performing coating thickness quality control.

22. The self referencing eddy current measurement system of claim 9, further comprising:
    a computer for receiving the compared signal and for converting the compared signal to a coating thickness value.

23. The self referencing eddy current measurement system of claim 22, wherein said computer is adapted to display the coating thickness value.

24. The self referencing eddy current measurement system of claim 22, wherein said computer is adapted to compare the coating thickness value with a cutoff thickness value for performing coating thickness quality control.

25. The self referencing eddy current measurement system of claim 22, wherein said computer is adapted to use a calibration curve to convert the compared signal to the coating thickness value.

26. The self referencing eddy current measurement system of claim 22, wherein said computer is adapted to use a plurality of calibration data to convert the compared signal to the coating thickness value.

27. The self referencing eddy current measurement system of claim 9, further comprising:
   an eddy current instrument which includes said comparison module; and
   a computer for receiving the compared signal and converting the compared signal to a coating thickness value.

28. A self referencing eddy current measurement method comprising:
   positioning an edge of an eddy current probe housing on a test object;
   energizing a test eddy current coil facing the test object, the test coil being situated on an edge of the probe housing;
   energizing a reference eddy current coil facing a reference sample, the reference sample and reference coil being situated in the probe housing;
   comparing a test signal from the test coil with a reference signal from the reference coil to produce a compared signal; and
   converting the compared signal to a coating thickness value.

29. The self referencing eddy current measurement method of claim 28, wherein said positioning step includes conforming an active face of the test coil to a surface of the test object.

30. The self referencing eddy current measurement method of claim 28, further comprising:
   displaying the coating thickness value.

31. The self referencing eddy current measurement method of claim 28, further comprising:
   comparing the coating thickness value with a cutoff value to determine whether the test object meets a predetermined standard.

32. The self referencing eddy current measurement method of claim 28, further comprising:
   calibrating the test coil and reference coil by measuring an uncoated substrate and a plurality of coated substrate samples, each sample having a known coating thickness, to generate a plurality of calibration data,
   wherein said converting step includes using the calibration data to convert the compared signal to the coating thickness value.

33. The self referencing eddy current measurement method of claim 32, further comprising:
   recalibrating the test coil and reference coil by repeating said calibrating step at a predetermined time interval.

34. The self referencing eddy current measurement method of claim 28, further comprising:
   calibrating the test coil and reference coil, said calibrating step including:
      measuring an uncoated substrate and a plurality of coated substrate samples, each sample having a known coating thickness, to generate a plurality of calibration data; and
      deriving a calibration curve from the calibration data,
      wherein said converting step includes using the calibration curve to convert the compared signal to the coating thickness value.

35. The self referencing eddy current measurement method of claim 34, further comprising:
   recalibrating the test coil and reference coil by repeating said calibration step at a predetermined time interval.

36. The self referencing eddy current measurement method of claim 28, wherein said energizing steps are responsive to a signal generated by a computer.

37. The self referencing eddy current measurement method of claim 28, wherein said converting step is performed using a computer.

38. The self referencing eddy current measurement method of claim 37, further comprising:
   displaying the coating thickness value using a computer.

39. The self referencing eddy current measurement method of claim 38, wherein said energizing steps are responsive to a signal generated by a computer.

* * * * *